(12) United States Patent
Magagnoli (10) Patent No.: US 10,792,158 B2
(45) Date of Patent: Oct. 6, 2020

(54) SPACER DEVICE FOR TREATING A JOINY OF THE HUMAN BODY

(71) Applicant: Cossington Limited, Kingston upon Thames (GB)

(72) Inventor: Augusto Magagnoli, Cervia (IT)

( * ) Notice: Subject to any disclaimer, the term of this patent is extended or adjusted under 35 U.S.C. 154(b) by 21 days.

(21) Appl. No.: 16/092,184

(22) PCT Filed: Apr. 10, 2017

(86) PCT No.: PCT/IB2017/052053
§ 371 (c)(1),
(2) Date: Oct. 8, 2018

(87) PCT Pub. No.: WO2017/178951
PCT Pub. Date: Oct. 19, 2017

(65) Prior Publication Data
US 2019/0159904 A1 May 30, 2019

(30) Foreign Application Priority Data

Apr. 11, 2016 (IT) .......................... 102016000036801

(51) Int. Cl.
*A61F 2/36* (2006.01)
*A61F 2/30* (2006.01)

(52) U.S. Cl.
CPC .......... *A61F 2/3609* (2013.01); *A61F 2/3662* (2013.01); *A61F 2002/3055* (2013.01);
(Continued)

(58) Field of Classification Search
CPC ........ A61F 2/3854; A61F 2/3859; A61F 2/38; A61F 2002/30649; A61F 2/3609; A61F 2/3662
See application file for complete search history.

(56) References Cited

U.S. PATENT DOCUMENTS

2012/0165760 A1    6/2012  Missling

FOREIGN PATENT DOCUMENTS

EP    2052700    4/2009
FR    2948012    2/2011
(Continued)

*Primary Examiner* — Jason-Dennis N Stewart
(74) *Attorney, Agent, or Firm* — Themis Law (57) ABSTRACT

An implantable modular spacer device to treat an infected articular seat includes a stem element, a head or ball element, and coupling elements between the stem element and the head that include a plurality of elongated teeth, placed at pre-established distances from each other, and a plurality of housing seats for the teeth. An implantable spacer device to treat a bone seat or joint seat or for the two-step treatment of infections of joint prostheses includes a joint component adapted to be inserted in an articular zone of the patient and having an external surface, a stem component adapted to be implanted in a bone or in a residual bone bed of a preceding joint prosthesis, and adjustable connection elements, wherein at least part of the external surface of the first portion of the stem component and at least part of the external surface of the joint component define a contact surface with the bone tissue or adapted for coupling with the bone tissue. The connection elements are placed between the joint component and the stem component to adjust the distance thereof, and the contact surface in the joint component and/or in the stem component has a plurality of recesses or housing a filling material that includes a pharmaceutical or medical substance, wherein the plurality of recesses affects or is substantially placed along the entire contact surface or in proximity thereto.

19 Claims, 4 Drawing Sheets

(52) U.S. Cl.
CPC ........... *A61F 2002/3068* (2013.01); *A61F 2002/30405* (2013.01); *A61F 2002/30616* (2013.01); *A61F 2002/30672* (2013.01); *A61F 2002/30677* (2013.01); *A61F 2002/30805* (2013.01); *A61F 2002/365* (2013.01); *A61F 2310/00011* (2013.01); *A61F 2310/00329* (2013.01); *A61F 2310/00353* (2013.01)

(56) References Cited

FOREIGN PATENT DOCUMENTS

| WO | 2009149296 | 12/2009 |
|---|---|---|
| WO | 2010015877 | 2/2010 |
| WO | 2016132200 | 8/2016 |

SPACER DEVICE FOR TREATING A JOINY OF THE HUMAN BODY

TECHNICAL FIELD OF THE INVENTION

The present invention regards a spacer device, of temporary and disposable type, for the treatment of a bone pathology, i.e. for example of a bone tissue subject to infection, or of a bone articulation of the human body affected by infection.

The present invention also regards a method for making one such spacer device.

STATE OF THE PRIOR ART

Very rarely, the articular bone can be infected following trauma or via microbial abscesses (e.g. dental) transported by the blood flow. In this case, the infected articular ends are surgically eliminated and in their place a spacer device is arranged with the function of restoring the articulation and freeing anti-infective medications onsite in order to defeat the infection. Once such actions is completed, the spacer device will be removed and substituted in its articular action by a final prosthesis.

It is known that the prostheses implanted within the human body can be subjected to infections.

In such case, the infected prosthesis must be removed from the implant site and before the implant of a new prosthesis it is necessary that the infection be defeated.

During such step, spacer devices are normally employed in order to maintain substantially unaltered the shape of the joint seat where the new prosthesis will be implanted.

One example of a spacer device is described in the international application WO2010/015877.

Such procedure is known as "two-step treatment" for the removal of an infected prosthesis and the implant of a new prosthesis.

The spacer devices usually used can have an external surface of porous type, possibly impregnatable with one or more pharmaceutical or medical substances to be released in the human body, at the anatomic area where their implant is provided.

In such spacer devices, the quantity of the pharmaceutical or medical substance which can be possibly impregnated along the porous external surface is limited by the depth and by the extension of the surface itself. In such case, the spacer device might not be able to ensure a release of the pharmaceutical or medical substance for a time period equal to that necessary for the complete healing of the infected seat.

In addition, in using the devices of known type, it is not possible to apply two or more pharmaceutical or medical substances that are different from each other, maintaining such substances separate from each other. Indeed, it is not easy, in a same spacer of known type, to use different substances in different, separate zones, placed along the coupling surface with the bone tissue of the patient.

There are then preformed spacer devices which are produced by casting in a mold a previously-made antibiotic bone cement, up to the hardening thereof and extracting, from the mold, the hardened spacer device, which is subsequently processed or finished in accordance with the requirements.

The patent application FR2948012 describes a device for the substitution of a permanent joint prosthesis comprising a stem and a head. The head, made of a material such as polyethylene, comprises, in its base directed during use towards the stem, at least two separate cavities. Such cavities allow the diffusion of a liquid and are provided with a kind of cap capable of blocking or limiting the outflow thereof. The connection between head and stem is made by means of a machine taper.

Alternatively, the surgeon can himself make a spacer during the operating step, by using molds, usually made of silicone with suitable geometry, which are filled with antibiotic bone cement, which is possibly admixed with a further antibiotic different from the first. Once the polymerization occurred, the surgeon extracts the spacer from the silicone mold, facilitated by the flexible nature of the latter material, and then proceeds with the implant, possibly refining the spacer if necessary.

Also in this case, it is not possible, or it is extremely difficult, for a surgeon to apply different pharmaceutical or medical substances in specific and separate portions of the spacer device, since the antibiotic bone cement cast in the mold is freely arranged within the same, substantially filling the entire volume thereof.

The United States patent application US2012/165760 describes a medical device implantable in the human body comprising one or more surface recesses adapted to receive a composition for the drug release. Such composition comprises a matrix and one or more active agents. Such surface recesses assume the configuration of elongated grooves which are extended, for example, along the length or circumference of the stem of the medical device.

The surgeon must therefore arrange a spacer device in which it is possible to position or apply one or more pharmaceutical or medical substances along specific portions of the device itself, in the scope of a solution that is easy to actuate.

In addition, there is the need to provide a spacer device that ensures the release of one or more pharmaceutical or medical substances for the entire time period provided for the treatment of the infected seat.

In addition, with respect to the devices of known type, there is the need to arrange a solution capable of allowing a certain modularity of the components that compose the spacer and the possibility to adjust the mutual position thereof, obtaining a device that is particularly effective, safe and inexpensive.

Finally, there is the need to arrange, in any case, a spacer device with predefined and correct shape and size, without the risk that the surgeon, having to directly make the spacer device in situ, will obtain an irregular shape or a shape incompatible with the actual anatomic needs of the patient, or in any case to be finished and processed before implant.

OBJECTS OF THE INVENTION

The task of the present invention is that of improving the state of the prior art.

In the scope of such technical task, one object of the present invention is to provide a spacer device for the treatment of an infected joint seat of the human body that is easy to use for the release of at least one pharmaceutical or medical substance.

A further object of the present invention is to provide a spacer device for the release of at least one pharmaceutical or medical substance in specific portions of the joint seat of the human body with which it is associated, also possibly for long time periods.

Another object of the present invention is to provide a spacer device having the possibility of adjusting the distance between its components, and possibly varying the shape and size thereof in accordance with the specific needs of a patient.

Another object of the present invention is to implement a spacer device which is easily adaptable to the different patient sizes.

In accordance with one aspect of the present invention, a spacer device is provided according to claim 1.

Also constituting an object of the present invention is a method for making a spacer device, according to claim 15.

The dependent claims refer to preferred and advantageous embodiments of the invention.

BRIEF DESCRIPTION OF THE DRAWINGS

Further characteristics and advantages of the present invention will be more evident from the detailed description of a preferred but not exclusive embodiment of a spacer device, illustrated by way of non-limiting example in the enclosed drawing tables in which:

figure is a side view of a spacer device according to the present invention in which the stem component of FIG. 7 is assembled with the joint component of FIG. 4, the latter being partially represented transparent;

FIG. 11 is a perspective view of the stem component according to the present invention.

EMBODIMENTS OF THE INVENTION

With reference to the figures, reference number 1 overall indicates a spacer device according to the present invention, in particular a spacer device for the treatment of an infected bone seat or joint seat.

According to another version, the spacer device according to the present invention is indicated in the two-step treatment of the infections of the joint prostheses.

In the illustrated embodiment, explicit reference will be made to a spacer for the treatment of a hip seat and/or for the substitution of hip prosthesis, even if it must be intended that the present invention can also be used for treating other types of bone seats and/or for the substitution of other prosthesis types, e.g. shoulder prostheses or seats, ankle, elbow, knee prostheses or seats, etcetera.

The spacer device according to the present invention is of temporary and/or disposable type.

With the term "temporary" it is intended that, once its treatment function is completed, together with its function of maintaining the space of the joint seat, the spacer device will be removed from the zone in question and substituted for example with a permanent prosthesis.

For such purpose, the spacer device carries out the function of maintaining the articular spaces as well treating the bone infection by freeing a quantity of at least one pharmaceutical or medical substance in the infected zone.

With regard to the latter aspect, the spacer is able to treat the infection underway by releasing at least one pharmaceutical or medical antibiotic substance, such as an antibiotic, in a specific/directed manner and in infinitesimal quantities, while the application of doses of antibiotic that are even quite high, but with methods that do not provide for the use of spacers, such as the washing of the infected site with high-dosage antibiotic solutions, does not allow obtaining the same results.

Studies conducted in the field have in fact shown that the bone tissue absorbs in a concentrated manner all the molecules of at least one pharmaceutical or medical substance or antibiotic (even only a few molecules) freed daily from the spacer. Naturally, this occurs if the antibiotic is released by the spacer in contact with or next to the bone tissue, in which case the infinitesimal quantity of antibiotic locally reaches the effective concentration for defeating the infection. For this reason, it is essential that the spacer is extended for the entire area of the infection, intending that if the infected prosthesis is a long prosthesis, a long spacer will be used, and if the infected prosthesis is a short one, a short spacer will be used. If a short spacer is a placed where a long prosthesis was previously implanted, part of the bone would not be treated with the at least one pharmaceutical or medical substance or with the antibiotic, thus allowing bacteria to be free to proliferate.

The spacer device according to the invention has a body shaped so as to be couplable, in a substantially complementary manner, to the joint seat with which it must be constrained.

The spacer device 1 comprises a first portion and a second portion, removable and adjustably connected to each other.

The first portion is a joint component 2 while the second portion is a stem component 3.

The stem component 3 is adapted to be fixed to a corresponding bone or residual bone bed of a preceding implant while the joint component 2 is adapted to be inserted in a corresponding articular zone of the patient.

The stem component 3 and the joint component 2 are connected by means of connection means, overall indicated with 4. The connection means 4 are of adjustable type.

Locking means are provided, adapted to fix the mutual position of the connection means 4, as will be better indicated hereinbelow.

Specifically, in one version of the invention, the stem component 3 is adapted to be inserted, during use, in the proximal portion of a femoral bone, in proximity to the hip articulation. In such version, the joint component 2 is instead to be housed, during use, in the articular zone of the cotyloid cavity (or acetabulum), at the hip articulation. The joint component 2, therefore, is anatomically comparable to the head of a femur.

In one version of the invention, within the joint component 2 and/or stem component 3, an internal reinforcement core can be provided, for example made of metal material or of another material with suitable mechanical characteristics.

The joint component 2 (or head) of the spacer device 1 according to the invention comprises a substantially spherical configuration.

In particular, in one version of the invention, the volume occupied by the joint component 2 corresponds with that of a spherical segment at one base.

The joint component 2, in one version of the invention, comprises an external surface E and a base 6. The external surface E is substantially spherical or corresponds with the surface of a spherical cap at one base, in particular the base 6.

The base 6 during use is directed towards the stem component 3 while the external surface E is during use directed towards the cotyloid cavity of the patient, considering the hip articulation as an example, or in any case it is directed on the opposite side with respect to the base 6.

The external surface E is composed of a first surface 5. The first surface 5 has substantially hemispherical shape.

In one embodiment, the first surface 5 is placed at the apical portion of the joint component 2 and occupies the surface of at least one apical hemisphere.

In a specific version, the first surface 5 occupies the surface of more than one hemisphere, in particular the surface of a spherical cap at one base. In this case, the first surface 5 continues beyond the equatorial plane Q of the joint component 2 and the base 6 has smaller area than that occupied by the base of a hemisphere.

By equatorial plane, it is intended a plane perpendicular to the symmetry axis A of the joint component 2 and passing through a diameter thereof.

In one version of the invention, the joint component 2, at the first surface 5 or at least at the first surface 5, has radius R1.

In one version of the invention, the joint component 2 comprises a lateral wall 7 of connection between the base 6 and the first surface 5.

In one version, the lateral wall 7 has a substantially frustoconical shape, in which one base of the frustoconical shape corresponds with the base 6 while the other base corresponds with the base of the spherical cap corresponding with the first surface 5.

In a further version, the lateral wall 7 has a shape substantially with second spherical cap, with two bases, in which one base of the second spherical cap corresponds with the base 6 while the other base corresponds with the base of the first spherical cap or spherical cap corresponding with the first surface 5.

In one version, the joint component, at the lateral wall 7, has radius R3, wherein R3 is equal to, greater or less than R1.

In a further version, the lateral wall 7 is tapered towards the base 6.

The joint component 2 comprises a first cavity 8.

The first cavity 8 has a substantially cylindrical shape that is extended within the joint component 2. The first cavity 8 has a progression substantially parallel with respect to the symmetry axis A of the joint component 2. In a specific version, the symmetry axis A corresponds both for the joint component 2 and for its first cavity 8.

In one version of the invention, the first cavity 8 departs from the base 6, creating an opening 10 in the latter that may be circular.

The first cavity 8 has an internal lateral wall 9 which, in one version of the invention, has a thread or nut screw.

The stem component 3 has a first portion 11.

The first portion 11 has a substantially elongated shape, adapted to be inserted during use in the medullary canal of an elongated bone, such as a femoral bone.

The first portion 11 is tapered starting from a first proximal end P of the stem component 3, towards a second distal end D of the stem component 3.

The first proximal end P is during use directed towards the joint component 2 while the second distal end D is during use adapted to enter more in depth into the medullary canal or in any case is opposite the first proximal end P.

The first portion 11 has, in one version, a substantially conical or frustoconical or pyramid frustum shape.

The second distal end D has a rounded shape, in order to prevent pressure or damaging points for the bone tissue with which it comes into contact during use.

In one version of the invention, the first portion 11 can comprise 4 faces, two substantially flattened faces 11A and 11B and two substantially curved faces 11C and 11D.

The two substantially flattened faces 11A and 11B are positioned on opposite sides with respect to a plane S of longitudinal symmetry of the first portion 11 or of the stem component 3.

The two substantially curved faces 11C and 11D are substantially perpendicular with respect to the plane S.

In one version of the invention, the curvature radius of the two substantially curved faces 11C and 11D is greater than the curvature radius of the two substantially flattened faces 11A and 11B.

In plan or side view, each substantially flattened face 11A or 11B has a substantially trapezoidal shape, with two longitudinal sides L1, L2 substantially corresponding with the length of each of the substantially flattened faces 11A and 11B, which converge towards a first base B1, placed at the second distal end D of the stem component 3, and a second base B2, of greater size than the first base B1.

The side L1 has smaller size than the side L2, such that the base B2 is tilted.

Analogously, a substantially curved face 11C has a substantially rectangular shape, with the sides of size corresponding to L1 and a base B3. The other substantially curved face 11D has a substantially rectangular shape, with the sides of size corresponding to L2 and a base B2 substantially of the same size as that of the face 11C.

The stem component also comprises an enlarged portion 12, placed at the first proximal end P of the first portion 11 and which departs from the latter.

The enlarged portion 12 is tapered towards the outside and departs from the area under the bases B2 of the faces 11A and 11B and from the bases of the faces 11C and 11D.

The enlarged portion 12 has, in one version, a substantially frustoconical or pyramid shape. In a further version, the enlarged portion 12 is enlarged, starting from the area under the bases B2 of the faces 11A and 11B and from the bases of the faces 11C and 11D, for a certain first section, before then narrowing up to a certain second section.

In fact, the stem component 3 has, considering the shape of its enlarged portion 12 together with the first portion 11, a substantially "L" shaped progression, or progression with obtuse angle.

The stem component 3 also comprises a shank 13.

The shank 13 departs from the enlarged portion 12.

In one version of the invention, the shank 13, the enlarged portion 12 and the first portion 11 are made of a single piece. In such a manner, an improved stability and mechanical strength of the stem component 3 is achieved as well as a greater simplicity of implant and manufacturing of the spacer device 1.

The shank 13 has a longitudinal symmetry axis F.

The longitudinal symmetry axis F of the shank 13 is tilted with respect to the longitudinal axis of the first portion 11.

Both such axes lie along the symmetry plane S of the stem component 3.

In one version of the invention, the longitudinal symmetry axis F during use coincides with the symmetry axis A of the joint component 2.

The shank 13 has a substantially cylindrical shape.

The shank 13 is adapted to be housed during use within the first cavity 8 of the joint component 2. Therefore, the shank 13 is adapted to be inserted, through the opening 10, in the first cavity 8 and then within the joint component 2.

The shank 13, in particular, is adapted to be connected with the joint component 2 and hence, actually, to determine the connection between the joint component 2 and the stem component 3.

The shank 13 in fact has a thread or screw corresponding with the thread or nut screw of the internal lateral wall 9 of the first cavity 8 of the joint component 2.

The thread or screw of the shank 13 and the thread or nut screw of the joint component are of rounded profile type.

For example, such profile is substantially similar to the unified profile of Edison type, or other similar profiles.

This solution allows, among the other advantages, obtaining a greater resistance to breakage and a greater moldability of the threads during production.

In addition, if such threads are made of plastic material, the rounded profile prevents cracks or pressure points from being created which could lead—if excessively stressed—to the breakage of the component on which such thread is present.

Profiles with greater pitch can also be provided, for increasing the coupling surface areas and hence increasing the coupling strength itself.

The first cavity 8 of the joint component 2 has size slightly greater than that of the shank 13, such that the latter can be housed and removably connected therewith.

In one version of the invention, the connection means 4 comprise the thread of the shank 13 and the thread or nut screw of the first cavity 8 of the joint component 2 and hence cause the removable and adjustable connection thereof with the stem component 3.

In particular, the connection means 4 allow adjusting the mutual position between the joint component 2 and the stem component 3.

In detail, due to the connection means 4 it is possible to vary the distance G (indicated in FIG. 10) between the stem component 3 and the joint component 2.

Figures 10, 11:
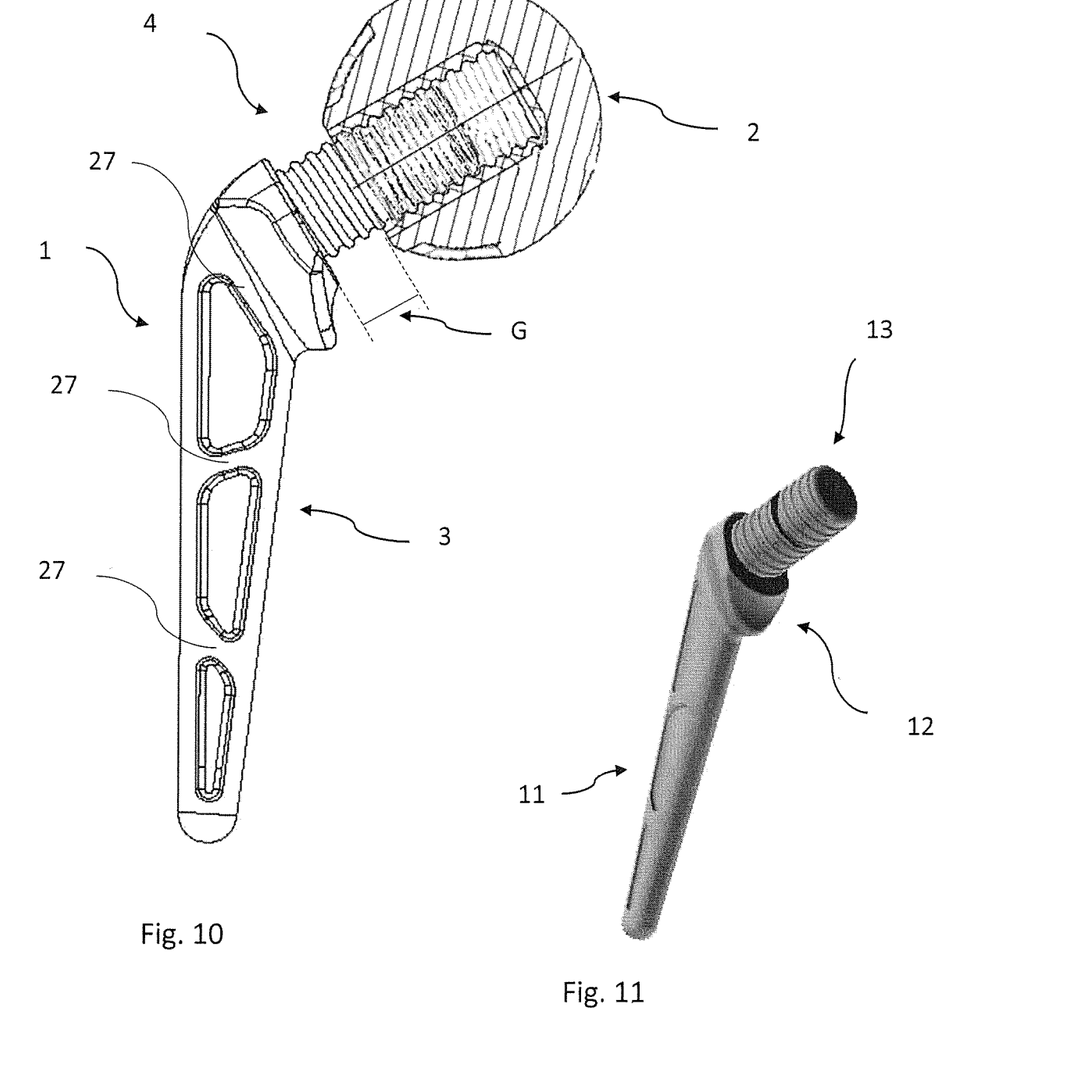

The distance G is adjustable. The distance G varies from a minimum of 0, when the joint component is in contact with the stem component 3, in particular with a base of its enlarged portion 12, to a maximum of G1. When G is equal to 0, the shank 13 is completely screwed within the first cavity 8 of the joint component 2.

When G is equal to G1, the distance G is maximum and the shank 13 is screwed in the first cavity 8 of the joint component to the point of maximum unscrewing. For distances of G greater than G1, the coupling or assembly stability of the spacer device 1 is not ensured.

In such a manner, the length of the so-called "neck" of the spacer device 1 according to the present invention is varied, and the latter is able to be precisely adapted to the surgical requirements and/or to the anatomy of the patient.

According to another aspect of the present invention, the shank 13 comprises a visual indicator (placed at G1) of the complete unscrewing position of the joint component 2 with respect to the stem component 3.

In other words, such visual indicator allows identifying, along the thread of the shank 13, the limit position beyond which the joint component 2 must not be unscrewed in order to avoid compromising the coupling of the spacer device according to the present invention.

More particularly, the visual indicator can comprise a band made along the external surface of the thread, for example made by means of a suitable paint, or another pigment type, with color quite visible to the operator in any situation, or by means of other equivalent techniques.

Such positions naturally represent the adjustment limit positions: the device can be adjusted in any intermediate position between the aforesaid limit positions.

The spacer device 1 according to the present invention is made of biologically compatible material; such biologically compatible material can be porous.

In one version of the invention, the biologically compatible material is adapted to be admixed and/or admixable with one or more pharmaceutical products, active and/or therapeutic principles, adapted to be released in the tissues of the patient adjacent to the device.

The materials for the spacer device according to the present invention can be selected from among metals, metallic alloys, metal-organic compounds, ceramics, glass and plastic.

Specifically, plastic can be selected from among thermoplastic polymers, such as acrylic resins, including all the acrylic alloys and copolymers, polyvinylchloride, polystyrene, polyethylene, ultra-high molecular weight polyethylene (UHMWPE), high or low density polyethylene, etcetera, polypropylene, polypropylene thermoformable via injection molding or by molding with blowing.

In one version of the invention, the biologically compatible material with which the spacer device is made comprises polymethylmethacrylate or a polymethylmethacrylate-based bone cement.

According to a further version of the present invention, the biologically compatible material can be a ceramic cement, such as calcium sulfate known as plastic or $CaSO_4$, which in addition to solidifying in limited times is able to release calcium ions.

In one version of the invention, the biologically compatible material with which the spacer device is obtained is permanent, i.e. it cannot be dissolved or degraded inside the human body.

In one version of the invention, the material of the spacer device according to the present invention can already comprise one of more first pharmaceutical products, active and/or therapeutic principles and, in addition, being porous, it can be further admixed, e.g. via impregnation, with further one or more pharmaceutical products, active and/or therapeutic principles, equivalent to or different from the first pharmaceutical products, active and/or therapeutic principles.

In a further version of the invention, the spacer does not comprise pharmaceutical products, active and/or therapeutic principles and is admixed, for example via impregnation, with one or more pharmaceutical products, active and/or therapeutic principles, at the time of implant in the patient.

The pharmaceutical products, active and/or therapeutic principles can comprise one or more antibiotics, antiseptics, antimycotics, chemotherapeutic principles, e.g. gentamicin, vancomycin, etcetera, or other active principles.

In one version, the connection means 4, in particular the thread of the shank 13 and the nut screw of the first cavity 8 of the joint component 2, are made of or at least covered with the above-described biologically compatible material.

In a further version, the connection means 4 are directly made in a single piece respectively with the shank 13 and in the joint component 2. Therefore, in this version, the connection means 4 are made of the same material as the components in which they are placed or present.

The faces 11A-11D of the stem component 3 and the external surface E of the joint component 2 determine at least one contact surface with the bone tissue and/or for the coupling of the spacer device with the bone seat or joint seat to be treated or with part thereof.

The at least one contact surface therefore has a shape substantially complementary to that of the bone seat or joint seat in which the spacer device 1 is positioned during use.

In one version of the invention, the joint component 2 comprises a plurality of recesses 14 positioned along the external surface E.

In one version of the invention, the plurality of recesses 14 has a substantially oval or polygonal shape with smoothed edges and/or corners.

In one version of the invention, the plurality of recesses 14 is radially positioned around the opening 10 of the joint component 2.

In particular, in such version, the plurality of recesses 14 is positioned at the lateral wall 7 of the joint component 2.

Figures 1, 2, 3:
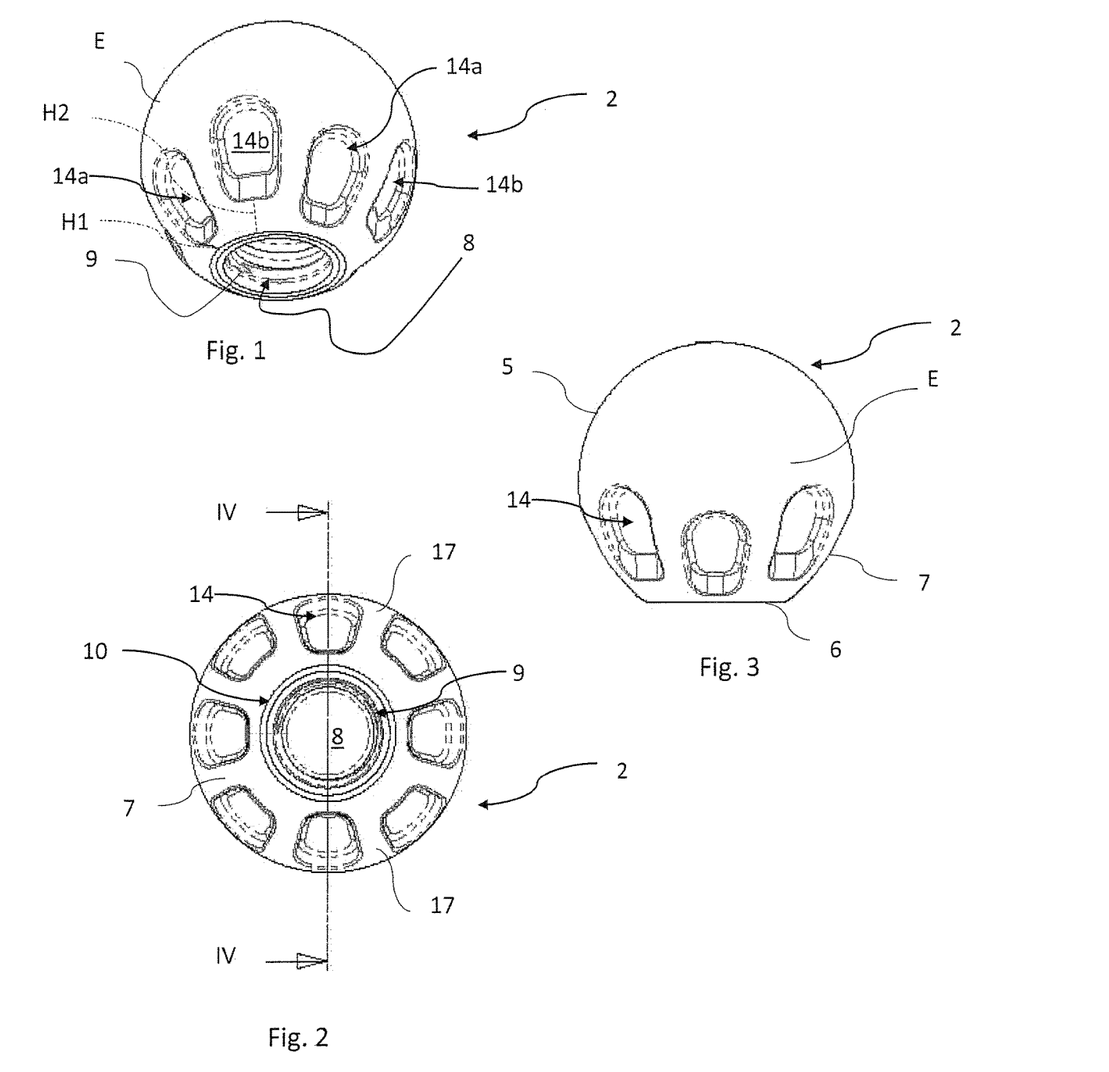
FIG. 1 is a perspective view of the joint component of a spacer device according to the present invention.
FIG. 2 is a bottom view of the joint component pursuant to FIG. 1.
FIG. 3 is a side view of the joint component pursuant to the preceding figures.
Figure 4:
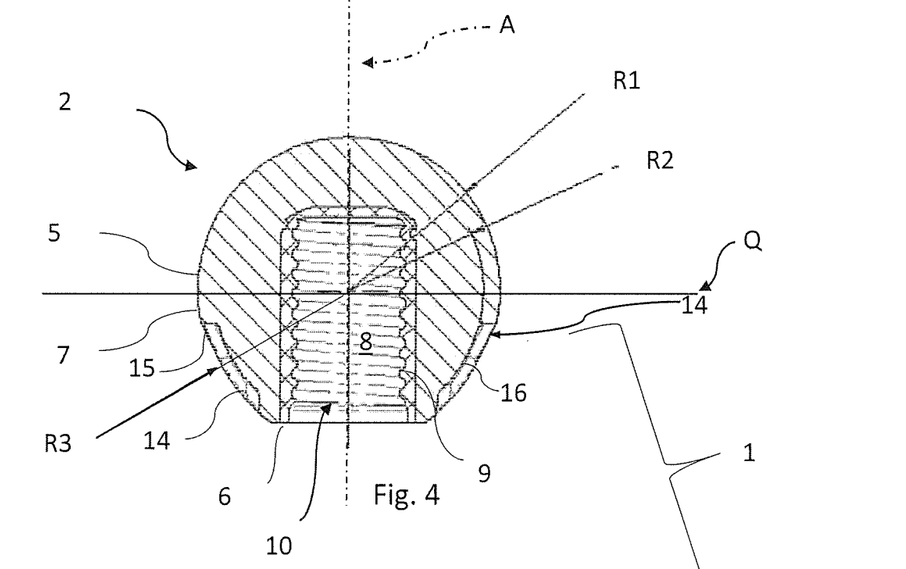
FIG. 4 is a section view of the joint component pursuant to the preceding figures, taken along the trace plane IV-IV of FIG. 2.

In one version of the invention, illustrated in the enclosed figures, each recess 14 (for example indicated with 14*a* in FIG. 1) is positioned offset in height with respect to the adjacent recesses (for example indicated with 14*b* in FIG. 1). In particular, the recesses 14*a* are positioned at the same height H1, with respect to the base 6 of the joint component 2. In addition, they are spaced by recesses 14*b* are that are placed at height H2 with respect to the base 6, in which H2 is greater than H1.

In a further version, not illustrated, the plurality of recesses 14 are all placed at the same height H1 or H2 with respect to the base 6.

In one version of the invention, the recesses 14 have a first size or width smaller than a second size or height, in which the first size or width is placed at the opening 10 or in a parallel manner with respect thereto while the second size or height is placed in a substantially perpendicular manner with respect to the opening 10 or to the base 6.

This specific arrangement of the plurality of recesses 14 of the joint component 2 neither affects nor compromises the possibility of articulation of the joint component itself within the bone articulation with which it is in contact or engaged.

Analogously, the stem component 3 comprises a plurality of recesses 24, analogous to the recesses 14 of the joint component 2.

In particular, the plurality of recesses 24 is placed along the substantially flattened faces 11A and 11B of the stem component 2.

In one version of the invention, the plurality of recesses 24 has a substantially trapezoidal or polygonal shape with smoothed edges and/or corners.

In one version of the invention, the plurality of recesses 24 is positioned in a complementary or adjacent manner along each face 11A or 11B. In such a manner, a kind of cell structure is created in which each cell is constituted by a recess 24.

Figure 7:
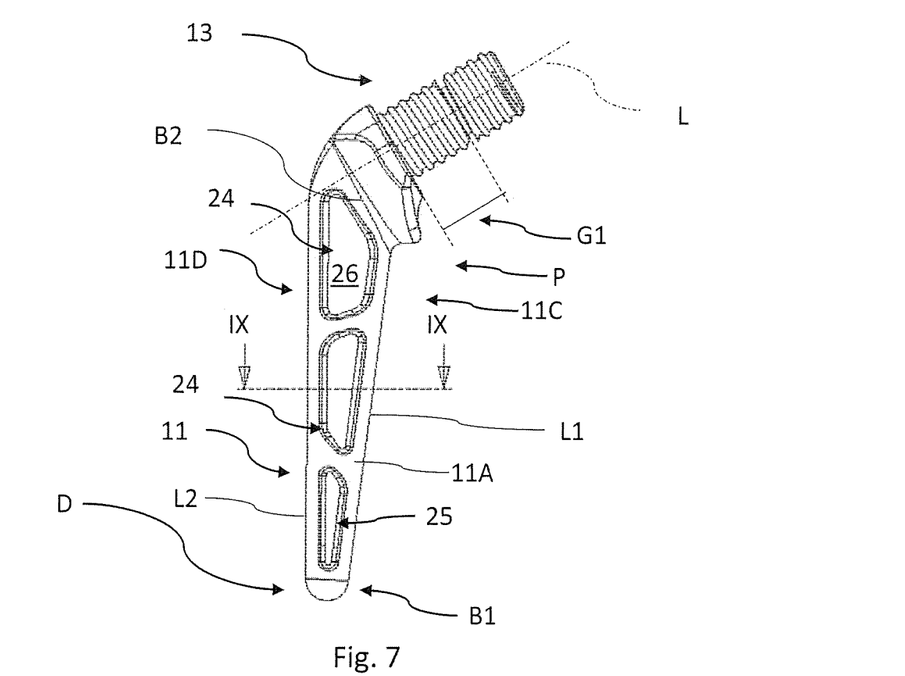
FIG. 7 is a side view of the stem component pursuant to FIG. 5.
Figure 8:
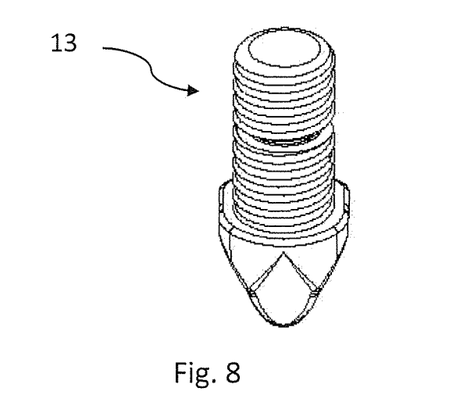
FIG. 8 is a top view of the stem component pursuant to the preceding figures.
Figure 9:
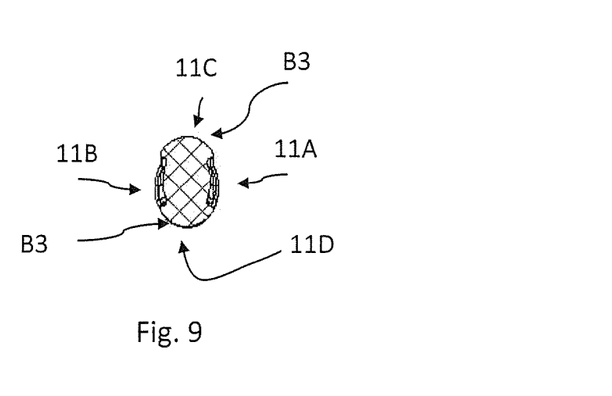
FIG. 9 is a section view of the stem component pursuant to the preceding figures, taken along the trace plane IX-IX of FIG. 7.

In one version of the invention, illustrated for example in FIG. 7, each recess 24 has a plan extension substantially corresponding to a part of the extension of the face 11A or 11B in which it is positioned.

In one version of the invention, the recesses 24 have a first size or width smaller than a second size or height, in which the second size or height is placed parallel to the symmetry plane S of the stem component 3 or to the longitudinal axis of the first portion 11.

Each recess 14, 24 can be extended more or less deeply within the joint component 2 or stem component 3. Nevertheless, the surfaces extension or opening of the recess 14, 24 is greater than its depth.

In such a manner, due to this specific shape, it is possible to completely fill each recess 14, 24, without risking that some parts of the same remain accidentally without filling material M. There is a risk of this happening, for example, when the recesses have greater depth than width or when the opening that they determine on the surface of the medical device is limited. Indeed, in these case, air bubbles could for example remain trapped within the recess and thus could prevent the correct filling of the latter.

Each recess 14, 24 has a perimeter wall 15, 25 that is extended respectively from the lateral wall 7 towards the interior of the joint component 2 or from the contact surface of the first portion 11 of the stem component 3. Each recess 14, 24 also comprises respectively a base wall 16, 26 which forms the base of each recess 14, 24. The perimeter wall 15, 25 is tilted towards the exterior in a manner so as to determine an opening of each recess 14, 24 of greater width than the width of its base wall 16, 26.

In this version, the base wall 26 of the recesses 24 is placed parallel to the symmetry plane S of the stem component 3.

In fact, the recesses 24 substantially occupy the entire width each face 11A, 11B, except for sections or ribs 27.

The sections 27, whose width is quite limited with respect to the plan width of the recesses 24, in the illustrated embodiment have a tilted and opposite progression, in which the first section 27, placed at the base B2 of the face 11A, 11B, has the same progression as the base B2. A third section 27 (which separates a second recess 24 from a third recess 24) will have an analogous progression while a second section 27 (which separates a first recess 24 from the second recess 24) will have opposite progression, and so forth.

The sections 27 are interposed between the recesses 24.

Analogously, sections 17 can be provided that are interposed between the recesses 14.

The sections 17 have a substantially radial progression with respect to the base 6 and/or to the opening 10 of the joint component 2.

The thickness of the sections 17, 27 is smaller than the width (i.e. respect to both the length and width) of each recess 14, 24. The thickness of the section 17, 27 is that size which is extended perpendicular to the greater size or extension thereof, the latter also termed length of the section.

The depth of the sections 17, 27 corresponds with that of the adjacent recesses 14, 24.

In one version of the invention, each face 11A, 11B comprises three recesses 24, as illustrated in the figures.

In one version of the invention, the base wall of each recess 14, 24 is recessed 3 mm with respect to the external surface E or to the lateral wall 7 of the joint component 2 or of the contact surface of the stem component 3 or of its first portion 11.

This specific arrangement of the plurality of recesses 24 of the stem component 3 allows the contact surface of the first portion 11 of the stem component 3 to be affected by the recesses 24 for most of such surface.

In addition, the particular shape and arrangement of the plurality of recesses 14, 24 causes a kind of localized "covering", as will be better described hereinbelow, of at least one portion of the joint component 2 and of at least part of the stem component 3.

In addition, the arrangement of the plurality of recesses 14 along the contact surface with the bone tissue or along the external surface E or along the lateral wall 7 or of the plurality of recesses 24 along the faces 11A and 11B of the stem component 3 can vary as a function of specific requirements.

In one version of the invention, not illustrated in the enclosed figures, recesses can also be present along the faces 11C and 11D of the stem component 3, entirely analogous to those recesses 24 present in the faces 11A and 11B.

Each recess 14, 24 forms a seat for housing a filling material M (visible for example in FIG. 5), possibly comprising at least one pharmaceutical or medical substance for the treatment of the infection present in the bone seat or joint seat with which the spacer device 1 is associated.

In one version of the invention, the filling material M is applied by the surgeon before the implant of the spacer device itself.

According to one aspect of the present invention, the filling material M is introduced or applied in at least one recess of the plurality of recesses 14 and/or 24.

In practice, the recesses 14, 24 act as a store for the storage of at least one pharmaceutical or medical substance, included in the filling material M, to be released inside the human body.

The filling material M can be made of biologically compatible material; such biologically compatible material can be porous.

In one version of the invention, such material can be ceramic, glass, plastic.

Specifically, the plastic can be selected from among thermoplastic polymers, such as acrylic resins, including all the acrylic alloys and copolymers, polyvinylchloride, polystyrene, polyethylene, ultra-high molecular weight polyethylene (UHMWPE), high or low density polyethylene, etcetera, polypropylene, polypropylene thermoformable via injection molding or by molding with blowing.

In one version of the invention, the biologically compatible material which constitutes the filling material M comprises polymethylmethacrylate or a bone cement, possibly polymethylmethacrylate-based.

In a preferred version, the filling material M comprises bone cement or PMMA or a PMMA-based bone cement.

According to a further version of the present invention, the biologically compatible material can be a ceramic cement, such as calcium sulfate known as plaster or $CaSO_4$, which in addition to solidifying in limited times is able to release calcium ions.

Such at least one pharmaceutical or medical substance present within the filling material M can be equivalent to or different from the pharmaceutical products, active and/or therapeutic principles possibly present in the spacer device 1 or in at least one of its components.

In addition, each recess can be filled with a filling material M having the same pharmaceutical or medical substance or different substances can be present in different recesses.

For example, due to the spacer device 1, it is possible—in a single device—to provide for the application of many different pharmaceutical or medical substances (such as for example two, three or four different antibiotics). Such substances, each housed in one or more recesses, is maintained separate from each other substance. In such a manner, the contact of different pharmaceutical or medical substances is prevented; such substances could be mutually eliminated or, if mixed, they could give rise to chemical-physical reactions that would compromise the effectiveness thereof.

In such a manner, the spacer device 1 according to the present invention can be personalized by the surgeon in accordance with the requirements of the patient. For example, the surgeon can apply, to the spacer device, all the necessary pharmaceutical or medical substances, housing each of these in one or more recesses, in order to keep them separate from each other but present in one same device, so as to transmit each substance into the affected area or so as to transmit the various substances into the bone seat or joint seat, without these being mixed together or applied together.

In one version of the invention, at least one recess might not comprise the filling material M or the at least one pharmaceutical or medical substance.

In such a manner, if necessary, by means of the recesses lacking filling material M or pharmaceutical or medical substance, it would also be possible to isolate or separate each pharmaceutical or medical substance in a specific zone, preventing to an even greater extent the contact or mixing or overlapping with a different substance housed in nearby or adjacent recesses.

The possibility of personalization is further increased, for the surgeon, considering that the material with which the spacer device 1 is made can be admixed or admixable with at least one further pharmaceutical or medical substance, equivalent to or different from those that will be—subsequently—housed in at least one recess, or possibly inserted in the filling material M in turn housed in at least one recess.

In such case, the possible addition of at least one pharmaceutical or medical substance present in at least one portion of the spacer device 1 could occur before the application of the filling material M and/or of the at least one pharmaceutical or medical substance, in a manner such that the latter is not mixed with that admixed with the material constituting the device itself.

The overall volume of the recesses 14, 24 is thus adapted for the time period estimated for treating the infection underway in the seat with which the spacer device is associated.

According to one version, the recesses 14, 24, and above all the recesses 24, are adjacent to each other.

The sections 17, 27, in addition to spacing and separating the recesses 14, 24, act as a reinforcement element for the joint component 2 and/or for the stem component 3.

For such purpose, the sections 17, 27 can be positioned at the portions of the spacer device 1 which, during use, are subjected to greater mechanical stresses, e.g. wear, bending, fatigue etc.

The filling material M can be the same material that constitutes the remaining part of the spacer device 1 according to the present invention.

Generally, if a spacer device has a wide contact surface with the bone tissue in relation to the volume of the device itself, the at least one recess can have a reduced depth with respect to its plan extension.

In addition, the single recesses 14, 24, in one version, can have different depths with respect to each other.

According to one version of the present invention, the recesses 14, 24 are arranged along the contact surface in a substantially uniform manner.

According to one aspect of the present invention, the filling material M is of hardening or solidifiable type.

In one version of the invention, the filling material can be prepared by the surgeon during the operating procedure.

Such filling material can lack pharmaceutical or medical substances and it can be added with the same based on the selection of the surgeon and on the patient needs.

In a further version of the invention, the aforesaid filling material can comprise at least one pharmaceutical or medical substance already arranged in the material that constitutes the filling material itself, and possibly can, during preparation, be admixed with a further substance.

According to one aspect of the present invention, the filling material, by virtue of the step of preparation and solidification to which it is subjected, can be porous.

The size of the pores possibly present in the filling material or in the spacer device 1 is such to prevent new bone growth during use within the same and, hence, within the spacer device, which as stated above is temporary.

One such configuration of the pores therefore facilitates the subsequent removal of the spacer device itself from the treated bone seat or joint seat, once its treatment function has been completed.

By way of example, the pores can have, in one version, dimensions on average smaller than 100 micron.

In such a manner, the pores present in the filling material M and/or in the spacer device 1 carry out a capillary function. The relative material, therefore, due to such capillarity, ensured by the size of the pores, can absorb at least one pharmaceutical or medical substance (present for example in liquid or solution form), maintain it at its interior and gradually release it over time.

The spacer device 1 is configured in a manner such that, when it is in use, the filling material is in contact with the bone tissues to be treated.

Figure 5:
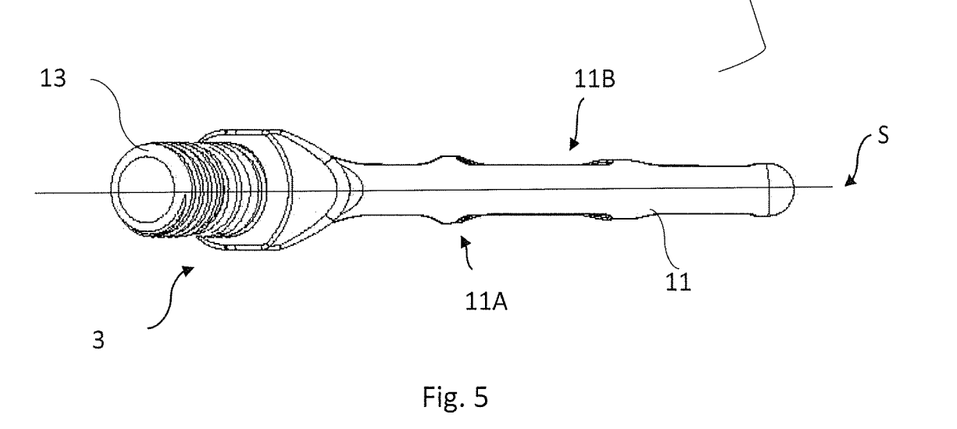
FIG. 5 is a front view of the stem component of a spacer device according to the present invention.
Figure 6:
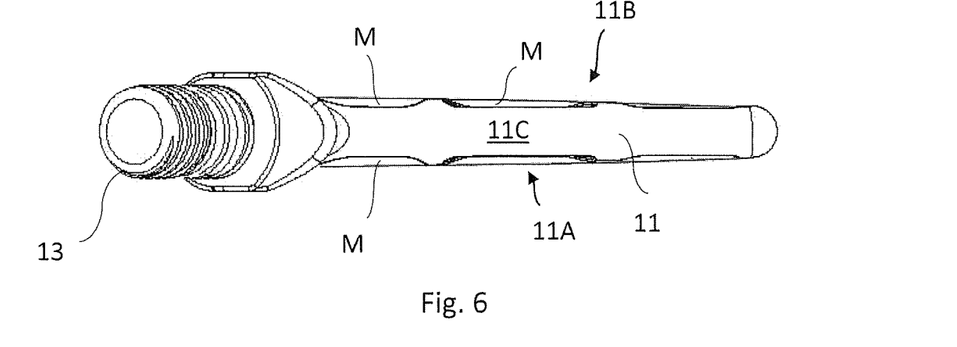
FIG. 6 is a front view of one version of a stem component of a spacer device according to the present invention.

According to one version, once the filling material M is positioned, it is flush with the contact surface, as is visible for example in FIG. 5. In such a manner, the external surface of the spacer device, during use adapted to be placed in contact with the bone tissue, or in any case in proximity thereto, is continuous and uniform, even in the presence of the filling material M. In one version of the invention, surface discontinuities are not present between the filling material M and the material that constitutes the stem component 3 and/or the joint component 2.

In the exemplifying version illustrated in the figures, the enlarged portion 12 does not comprises recesses 24.

Such aspect facilitates the strength of the structure of the stem component 3.

In general, the overall volume of the recesses 14 and/or 24 can be comprised between 1%-80%, with respect to the overall volume of the joint component 2 and/or of the stem component 3.

The higher percentage can be obtained when the material constituting the body of the spacer device is per se resistant to loads and to stresses, even if being provided with many recesses (and hence when the percentage of volume occupied by the material of the body is less than the "empty" volume relative to the recesses).

This can occur, for example, in one version of the invention, when the material which constitutes the body of the spacer device is a metal or a material with similar mechanical strength performances.

Alternatively, the overall volume of the recesses 14 and/or 24 can be comprised between 2% and 30% of the overall volume of the joint component 2 and/or of the stem component 3. Such percentage—less than that described above—can be used for example in one version of the invention, when the spacer device is made of a plastic material, such as PMMA or a PMMA-based bone cement.

One characteristic of the spacer device according to the present invention is that, even if in the presence of a high volume of recesses, the same do not alter the final shape of the device itself.

Therefore, the spacer device maintains an overall predefined or preformed shape—even in the presence of the at least one recess—in a manner such that the final form of the same has the advantages of the preformed devices of conventional type.

Indeed, the recesses, when they are filled with the filling material, recreate the overall or final form of the spacer device without requiring complicated or further working by the surgeon, who otherwise would be obliged to check the congruence of the surfaces created thereby with the filling material, with respect to the actual anatomic and/or articulation needs of the patient.

For example, in one version of the invention, the recesses can be filled with the filling material and closed with the same in order to define a flat external surface, or in any case a surface that lacks discontinuities.

In such case, the opening of the at least one recess is flush with the surface of the component of the spacer device or it is flush with the external edge of the sections 17, 27.

In such a manner, when the surgeon fills such recesses, he/she can flatten the outermost surface of the filling material contained therein, also with a spatula, still obtaining an overall defined final shape of the spacer device that reflects the anatomic and/or articulation needs of the patient.

The area occupied by the external surface of the at least one recess, in one version of the invention, has values comprised between 10% and 80%, when positioned on a surface that is substantially flat and/or on a surface that is at least partially curved of the spacer device in question.

For example, each recess can have an external surface corresponding to ½ to ¼ or even ⅙ to ⅛ of the surface of the face or of the surface on which it is present, for example of the face 11A or 11B of the stem component 3.

As stated, the recesses 14, 24 are flat and positioned at the interface with the bone tissue, in a particular manner, for example, for the stem component 3.

In one version of the invention, the filling material M is a fluid and/or pasty mass, obtained by joining with bone cement one or more pharmaceutical or medical substances, such as one or more antibiotics, for example.

In such a manner, in the version in which the filling material M comprises bone cement and the material with which the spacer device 1 is made is bone cement, the fluid bone cement of the filling material M is cast with the bone cement of the spacer device 1, making a perfect joining between the same. In such a manner, there is no risk, for the patient, that the filling material M will be detached from the respective spacer device, once the latter is implanted in the human body.

In addition, the flat profile of the recesses 14, 24, as well as the presence of the sections 17, 27, which are brief continuous sections, allows a facilitated filling of the recesses themselves with the filling material M. In such a manner, as stated, one is able to easily level the latter with the external surface of the spacer device 1 or with the external surface of the sections 17, 27, for example due to the aid of a simple spatula. Such alignment is important for avoiding possible over-thicknesses or discontinuities of fresh cement added by the doctor, with the consequent impossibility of inserting the spacer device in the proper cavity or bone seat, such as the diaphyseal canal for the stem component 3.

A further aspect of at least one version of the present invention is that the spacer device 1 carries out the mechanical function required for its use. Therefore, the material that constitutes it must be able to support the loads applied by the patient. Such aspect however does not regard the filling material M, whose object is not structural or mechanical but rather only that of vehicle for the at least one pharmaceutical or medical substance.

Consequently, the filling material M can comprise, in one version of the invention, more antibiotic than what would be possible to insert in the material of the spacer device, indeed because—unlike the latter—it does not have to exert mechanical strength.

The present invention then regards a method for making a spacer device 1.

The aforesaid method, initially, provides for providing a joint component 2 and a stem component 3.

Subsequently, the method provides for filling at least one of the plurality of recesses 14, 24, introducing at least one filling material M within the same.

Preferably, the method can comprise a step of admixing with the filling material at least one pharmaceutical or medical substance.

Subsequently, there can be a step of solidifying the filling material.

At the end of the solidification, a single body is formed, between the filling material and the component in which it was applied.

The material constituting the spacer device is refractory with respect to the bacterial colonization.

Therefore, due to the presence of the plurality of recesses 14, 24, the spacer device allows treating the infection underway in the insertion seat.

The at least one pharmaceutical or medical substance present in the filling material M can be gradually released, in a substantially uniform manner.

As stated, the various recesses are independent from each other, and allow storing one or more pharmaceutical or medical substances, possibly different from each other, maintaining them separate in specific portions of the spacer device itself.

The method according to the present invention can for example comprise the step of housing, in at least some of the recesses 14, 24, the filling material M comprising at least one pharmaceutical or medical substance, wherein such housing step is constituted by the steps of housing, in at least one first recess, the filling material M comprising a first pharmaceutical or medical substance and of housing, in at least one second recess, the filling material M comprising a second pharmaceutical or medical substance, wherein the at least one first recess is different or separate from the at least one second recess and wherein the first pharmaceutical or medical substance is different from the second pharmaceutical or medical substance.

In addition, steps can be provided for housing, in at least one third recess, the filling material M comprising a third pharmaceutical or medical substance and/or for housing, in at least one fourth recess, the filling material M comprising a fourth pharmaceutical or medical substance, wherein the at least one third recess is different or separate from the possible at least one fourth recess (and from the at least one first and second recess) and wherein the third pharmaceutical or medical substance is different from the possible fourth pharmaceutical or medical substance (and from the first and second pharmaceutical or medical substance), and so forth.

In a further version, the method comprises a step of leveling the filling material M, bringing it flush with the external surface of the joint component 2 and/or of the stem component 3, for example by means of the aid of a spatula or an analogous instrument. According to one aspect of the present invention, as stated, the spacer device according to the present invention can comprise locking means for locking the position between the joint component 2 and the stem component 3.

Such position is that desired by the surgeon and/or required by the specific surgical or anatomic needs.

The locking means comprise at least one glue means. Such glue means is applied on at least part of the connection means 4 in order to lock, glue or weld the mutual position thereof.

As will be clarified hereinbelow, in one version of the invention, the glue means, applied and allowed to act for a certain time period, dissolve the surface layers of the biologically compatible material of the coupling surfaces of the connection means 4, i.e. the complementary threads of the shank 13 and of the nut screw of the joint component 2, once they have been brought into contact and adjusted.

According to such aspect, the method according to the invention can provide for a step of distributing or applying a predetermined quantity of glue means on at least one of the surfaces of the connection means 4.

In one version, such connection means 4 are made of the biologically compatible material comprising polymethylmethacrylate or a polymethylmethacrylate-based bone cement.

The glue means can be of a different nature. For example, acrylic bone cement or cyanoacrylic glue can be used; it is also possible to use an organic solvent or a mixture of multiple components such as chloroform, methylmethacrylate, ethyl acetate, dichloromethane and not only or at least one of the same. Of course, whatever glue means is used, it must be stable and biocompatible.

Such step of distributing the glue means is carried out, in a particular version, by filling the cavity 8 of the joint component 2 with the glue means itself.

The glue means can then be available, for example, in a suitable phial or container, which is used directly by the surgeon during the implant procedure.

Subsequently, in such example, a step can be provided for applying a closure cap on the cavity 8, in order to prevent dispersing the glue means.

Such closure cap, according to one version, neither obstructs nor is engaged with the first threads of the nut screw.

Hereinbelow, the method provides for a step of immediately coupling the two parts, or a step of waiting a predetermined time interval, e.g. about one minute, in order to allow the glue means to start to act, for example starting to dissolve the polymethylmethacrylate.

Once such time interval has passed, the closure cap is removed, the shank 13 is inserted within the cavity 8 by screwing the thread of the shank 13 in the nut screw present in the cavity 8 up to the desired distance G or into the desired position.

In such a manner, as stated, the distance of the neck of the spacer device 1 is adjusted.

Finally, a step can be provided for waiting a further predetermined time interval, in order to allow the mutual stable fixing of the coupling surfaces. During such step, it can be advisable to not alter the coupling position of the components of the spacer device.

Such predetermined time interval can for example be about an hour or at least one hour.

In this time interval, the joint component 2 and the stem component 3 are mutually welded, making a fixing that is rigid, strong and safe over time.

Such locking therefore occurs in a quick, precise, simple and inexpensive manner, without the use of specific mechanical locking means or other costly systems or hard-to-use systems.

According to a further version, the glue means can be applied on both coupling surfaces of the connection means 4, rather than just one.

According to a further aspect of the present invention, the spacer device 1 can comprise at least one specific diagnostic or measurement device, not illustrated in the figures, housed within one of the recesses 14, 24.

By way of example, such diagnostic or measurement device could comprise a biomedical/biological micro-electromechanical system, such as a biosensor, capable of carrying out detections of chemical-physical type. One such biosensor, which corresponds with a chip, could comprise a miniaturized circuit in turn comprising an accelerometer and/or a thermometer and/or a load cell and/or sensors adapted to detect further physical quantities of different type.

The chip to be associated within a spacer device can be selected as a function of the specific use requirements and of the type of detections to be carried out.

By associating such chip with the spacer device 1, it is therefore possible to detect the use conditions of the device itself, with reference for example to the accelerations and/or to the static or dynamic loads to which it is subjected, to the temperature of the bone seat or joint seat in which it is implanted, etcetera.

According to a further aspect, the biosensor could comprise an integrated interface for the transfer of the detected data.

By way of example, the biosensor could comprise data transmission means for allowing the detection in real time of the use conditions of the spacer device with which it is associated, thus allowing the monitoring of the operation of the device itself.

In addition, the method according to the invention can comprise the steps of associating the joint component 2 with the stem component 3 and adjusting the distance between the joint component 2 and the stem component 3 by means of the connection means 4. In particular, such step provides for screwing the joint component 2 on the joint component 3 up to a specific distance G therefrom.

In such case, the surgeon can select the distance G most adapted to the specific surgical and/or anatomic requirements of the patient.

In one version of the invention, the joint component 2 can be provided in multiple dimensions or sizes. For example, different joint components 2 can be provided, with shape substantially equal, but each having a different diameter from that of another joint component 2. For example, the present invention can comprise a kit with two or more joint components, in which a first joint component has a diameter S1 while a second joint component has a diameter S2, in which S1 is smaller than S2, and so forth.

In such a manner, among the various joint components, one is selected which is best adapted to the surgical requirements and to the anatomy of the patient.

Analogously, in one version of the invention, the stem component 3 can be provided in multiple dimensions or sizes. For example, different stem components 3 can be provided, with shape substantially equal, but each having for example a different length or a different thickness from that of another stem component 3. For example, the present invention can comprise a kit with two or more stem components, in which a first stem component has a length Y1 and/or a thickness Z1 while a second stem component has a length Y2 and/or a thickness Z2, wherein Y1 is less than Y2, Z1 is less than Z2, and so forth.

Also in this manner, among the various stem components one is selected that is best adapted to the surgical requirements and to the anatomy of the patient.

According to the present invention, due to the characteristics of the connection means 4, each stem component 3 can be associated with each joint component, and vice versa, in order to obtain the maximum modularity and/or adaptability of the spacer device according to the present invention.

As is clear, the personalization of the spacer device 1 is maximal, since the surgeon can also select the at least one pharmaceutical or medical substance to be inserted in the recesses of the device, the other possible substances present in the device itself, as well as the size and the distance between the various constituent components.

The invention thus conceived is susceptible to numerous modifications and variations, all falling within the scope of the inventive concept.

The characteristics presented for one version or embodiment can be combined with the characteristics of another version or embodiment, without departing from the protective scope of the present invention.

In addition, all the details can be substituted by other technically equivalent elements. In practice, the materials used, as well as the contingent shapes and sizes, can be of any type in accordance with requirements, without departing from the protective scope of the following claims.

The invention claimed is:

1. A spacer device, implantable in a human body for treatment of an infected bone seat or joint seat or for a two-step treatment of infections of a joint prosthesis, comprising:

a joint component;
a stem component; and
connection elements,
wherein said joint component is adapted to be inserted in an articular zone of a patient,
wherein said stem component is adapted to be implanted in a bone or in a residual bone bed of a preceding joint prosthesis,
wherein said joint component has an external surface,
wherein said stem component comprises a first portion having a substantially elongated shape,
wherein at least part of an external surface of the first portion of said stem component and at least part of an external surface of said joint component are adapted to define a contact surface with bone tissue or are adapted to be coupled with the bone tissue,
wherein said connection elements are placed between said joint component and said stem component and are configured to enable adjusting a distance therebetweeen,
wherein said contact surface present in said joint component and in said stem component comprises a plurality of recesses for housing at least one filling material comprising at least one pharmaceutical or medical substance,
wherein said plurality of recesses is placed substantially along the contact surface, and
wherein each recess of said plurality of recesses has a planar surface extension and a depth,
wherein said planar surface extension is greater than the depth, each recess having a perimeter wall, which is respectively extended towards an interior of said joint component or of said stem component, and a base wall, which forms a base of each recess and determines the planar surface extension or an opening of each recess.

2. The spacer device according to claim 1, wherein said joint component comprises a base, wherein said external surface is essentially spherical or is shaped to mate with a surface of a spherical cap with the base, and wherein said base is adapted to be directed towards said stem component.

3. The spacer device according to claim 2, wherein said external surface is composed of a first surface of essentially hemispherical shape and radius, wherein said first surface s placed at an apical portion of the joint component, wherein said external surface is composed of a lateral wall, and wherein said lateral wall connects said base to said first surface.

4. The spacer device according to claim 3, wherein said plurality of recesses is positioned at said lateral wall of said joint component, and/or wherein each recess of said plurality of recesses is positioned offset height-wise with respect to adjacent recesses, and/or wherein some first of said recesses are positioned at a same first height, with respect to said base of the joint component, and wherein some second of said recesses, placed at a second height with respect to said base, are staggered with said some first of said recesses, wherein said second height is greater than or equal to said first height.

5. The spacer device according to claim 1, wherein said joint component comprises a first cavity, which is extended from said base, determining an opening in said base, and wherein said first cavity is adapted to house a shank of said stem component.

6. The spacer according to claim 5, wherein said joint component comprises said recesses, wherein said recesses have a first size or a width less than a second size or a height, and/or wherein said recesses have a substantially oval or polygonal shape with rounded edges and rounded corners, and/or wherein said first size or said width of said recesses is placed at the opening of the first cavity while the second size or said height of said recesses is placed in a manner substantially perpendicular to the opening of the first cavity, and/or wherein said plurality of recesses is radially positioned around the opening of the first cavity.

7. The spacer device according to claim 5, wherein said connection elements comprise a first thread and a first nut screw, wherein said first cavity has an internal lateral wall which has a second thread or second nut screw, and wherein said shank comprises a third thread corresponding to the second thread or second nut screw.

8. The spacer device according to claim 1, wherein said first portion comprises two essentially flattened faces and two essentially curved faces, wherein said two essentially flattened faces are positioned on opposite sides with respect to a longitudinal symmetry plane of said stem component, and wherein said plurality of recesses is placed at least along said essentially flattened faces.

9. The spacer device according to claim 8, wherein in plan or side view, each substantially flattened face has an essentially trapezoidal shape, with a first and a second longitudinal sides essentially corresponding to a length of each of said essentially flattened faces, which converge towards a first base, placed at a distal end of the stem component, and a second base, of a size greater than said first base, wherein said first longitudinal side has a size or length less than said second longitudinal side, such that said base is tilted.

10. The spacer device according to claim 8, wherein said stem component and/or its faces comprise said plurality of recesses, wherein said recesses are adjacent to each other and have an essentially trapezoidal or polygonal shape with rounded edges and/or corners, and/or wherein said recesses have a first size or width less than a second size or height, and/or wherein said base wall of each recess is placed parallel to a symmetry plane of said stem component.

11. The spacer device according to claim 8, wherein said recesses occupy essentially an entire area of each face and are delimited by sections or ribs that are projecting with respect to the base wall.

12. The spacer device according to claim 11, wherein said sections or ribs have a width that is less than both a width and a length of said recesses.

13. The spacer device according to claim 1, wherein said spacer device and/or said filling material is made of a biologically compatible material, admixed and/or admixable with one or more pharmaceutical products, active and/or therapeutic principles, adapted to be released in tissues of the patient adjacent to the spacer device, wherein said biologically compatible material is selected from the group consisting of metals, metallic alloys, organic metals, ceramic, glass, plastic, thermoplastic polymers, acrylic resins, acrylic alloys and copolymers, polyvinylchloride, polystyrene, polyethylene, ultra-high molecular weight polyethylene (UHMWPE), high or low density polyethylene, polypropylene, polypropylene thermoformable via injection molding or by molding with blowing, polymethylmethacrylate or a polymethylmethacrylate-based bone cement, a ceramic cement, and/or wherein said filling material is of hardening or solidifiable type.

14. A method of obtaining a spacer device, implantable in a human body for a treatment of an infected bone seat or joint seat or for a two-step treatment of a infections of a joints prosthesis, according to claim 1, comprising the following steps:
   arranging a joint component, adapted to be inserted in an articular zone of a patient, a stem component, adapted to be implanted in a bone or in a residual bone bed of a preceding joint prosthesis, and connection elements, placed between said joint component and said stem component and configured to enable adjusting a distance therebetween, wherein a contact surface present in said joint component and in said stem component comprises a plurality of recesses, wherein said plurality of recesses are placed substantially along the contact surface, wherein each recess of said plurality of recesses has a planar surface extension and a depth, wherein said planar surface extension is greater than the depth, each recess having a perimeter wall, which is respectively extended towards an interior of said joint component or of said stem component, and a base wall, which forms a base of each recess and determines the planar surface extension or an opening of each recess;
   positioning a shank of said joint component in a first cavity of said joint component;
   providing a filling material;
   housing, in at least some of said recesses, a filling material comprising at least one pharmaceutical or medical substance; and
   adjusting the distance between said joint component and said stem component.

15. The method according to claim 14, wherein said step of housing said filling material comprises applying or inserting or introducing said filling material into at least some of said recesses.

16. The method according to claim 14, further comprising a step of locking a mutual position of said connection elements by way of an application of locking means, said locking means comprising at least one adhesive.

17. The method according to claim 14, wherein said step of housing, in at least some of said recesses, the filling material comprising at least one pharmaceutical or medical substance, comprises the steps of housing, in at least one first recess, said filling material comprising a first pharmaceutical or medical substance and of housing in at least one second recess said filling material comprising a second pharmaceutical or medical substance, wherein said at least one first recess is different or separate from said at least one second recess, and wherein said first pharmaceutical or medical substance is different from said second pharmaceutical or medical substance.

18. The method according to claim 17, further comprising the steps of housing, in at least one third recess, said filling material comprising a third pharmaceutical or medical substance and/or of housing, in at least one fourth recess, said filling material comprising a fourth pharmaceutical or medical substance, wherein said at least one third recess is different or separate from said at least one first or said at least one second recess, and wherein said third pharmaceutical or medical substance is different from said first or said second pharmaceutical or medical substance.

19. A kit for making a spacer device, implantable in a human body for a treatment of an infected bone seat or joint seat or for a two-step treatment of infections of a joint prosthesis according to claim 1, comprising:
- at least two stem components having sizes or dimensions different from each other;
- at least two joint components having sizes or dimensions different from each other;
- at least one filling material; and
- connection elements,
- wherein each of said joint components is adapted to be inserted in an articular zone of a patient,
- wherein each of said stem components is adapted to be implanted in a bone or in a residual bone bed of a preceding joint prosthesis,
- wherein each of said joint components has an external surface,
- wherein each of said stem components comprises a first portion having a substantially elongated shape,
- wherein at least part of an external surface of the first portion of said stem component and at least part of an external surface of said joint component are adapted to define a contact surface with bone tissue and/or is adapted to couple with the bone tissue,
- wherein said connection elements are placed between said joint component and said stem component and are configured to enable adjusting a distance therebetween, said contact surface present in said joint component and in said stem component comprising a plurality of recesses for housing said at least one filling material comprising at least one pharmaceutical or medical substance,
- wherein said plurality of recesses is placed substantially along the contact surface, each recess of said plurality of recesses having a planar surface extension and a depth, and
- wherein said surface extension is greater than the depth, each recess having a perimeter wall, which is respectively extended towards an interior of said joint component or of said stem component, and a base wall, which forms a base of each recess and determines the planar surface extension or the opening of each recess.

* * * * *